United States Patent [19]
Fujieda

[11] Patent Number: 5,889,576
[45] Date of Patent: Mar. 30, 1999

[54] OPHTHALMIC APPARATUS

[75] Inventor: Masanao Fujieda, Toyohashi, Japan

[73] Assignee: Nidek Co., Ltd., Gamagori, Japan

[21] Appl. No.: 106,716

[22] Filed: Jun. 29, 1998

[30] Foreign Application Priority Data

Jun. 30, 1997 [JP] Japan ..................................... 9-190690

[51] Int. Cl.$^6$ .................................................... A61B 3/10
[52] U.S. Cl. .......................................................... 351/208
[58] Field of Search ..................................... 351/205, 206, 351/208, 211, 212, 221

[56] References Cited

U.S. PATENT DOCUMENTS 5,463,430 10/1995 Isogai et al. .
5,500,697 3/1996 Fujieda ..................................... 351/212

FOREIGN PATENT DOCUMENTS

A-6-46999 2/1994 Japan .

*Primary Examiner*—George Manuel
*Attorney, Agent, or Firm*—Oliff & Berridge, PLC

[57] ABSTRACT

An ophthalmic apparatus including a measuring device for measuring or examining an eye to be examined utilizing reflection of a luminous flux projected into the eye through a pupil, the ophthalmic apparatus comprising a moving device for moving the measuring device relative to the eye, a target projecting device for projecting an alignment target onto a cornea of the eye, a target detecting device for detecting an image of the alignment target, a photographing device for photographing an image of an anterior part of the eye, a pupil position detecting device for detecting a position of the pupil by signals transmitted from the photographing device, a judging device for determining a reference point for alignment based on information on the position of the pupil detected by the pupil position detecting device and the image of the alignment target detected by the target detecting device and an instructing device for giving instructions for making the moving device move based on the reference point determined by the judging device.

16 Claims, 5 Drawing Sheets

OPHTHALMIC APPARATUS

BACKGROUND OF THE INVENTION

1. Field of the Invention

The present invention relates to an ophthalmic apparatus, and more particularly to the ophthalmic apparatus suitable for measuring a refractive power of an eye to be examined, photographing the eye, or the like.

2. Description of Related Art

Conventionally, regarding a method of an alignment of an eye to be examined utilized in an ophthalmic apparatus, one widely known method is to detect or observe an image of a target projected onto a cornea of the eye to be examined, and thereby place a corneal center and the apparatus at positions having a predetermined positional relationship with respect to each other. Referring to an apparatus, for example an automatic eye refractive power measuring apparatus or the like, which projects a measurement luminous flux into the eye and detects a reflected luminous flux from a fundus of the eye with a photo-detector, it is required that the measurement luminous flux or the reflected luminous flux to pass the pupil being appropriate in size for measurement. Generally, positions of a corneal center and a pupil center of one eye approximately correspond to each other. There may be cases, however, where the deviation from each other is considerably big. In these cases, if an alignment is done with respect to the corneal center of the eye, the measurement luminous flux (the reflected luminous flux) is likely to eclipsed by an iris. Due to this eclipse, the measurement luminous flux may not be reflected, which is necessary to carry out the measurement, and measurement errors are easily to be caused.

In addition, a size of a pupil varies depending on brightness of a sight and individual variation. In the case of an eye having a pupil small in size, even if the amount of deviation between the corneal center and the pupil center is relatively small, a measurement based on an alignment with respect to the corneal center easily results in errors for the same reason mentioned above.

SUMMARY OF THE INVENTION

The present invention has been made in view of the above circumstances and has an object to overcome the above problem and to provide an ophthalmic apparatus capable of minimizing occurrence of errors as well as obtaining highly accurate results, upon measuring an eye refractive power of the eye or photographing the eye, regardless of deviation between the corneal center and the pupil center or individual differences in pupil size.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus including measuring means for measuring or examining an eye to be examined utilizing reflection of a luminous flux projected into the eye through a pupil, the ophthalmic apparatus comprises moving means for moving the measuring means relative to the eye, target projecting means for projecting an alignment target onto a cornea of the eye, target detecting means for detecting an image of the alignment target, photographing means for photographing an image of an anterior part of the eye, pupil position detecting means for detecting a position of the pupil by signals transmitted from the photographing means, judging means for determining a reference point for alignment based on information on the position of the pupil detected by the pupil position detecting means and the image of the alignment target detected by the target detecting means and instructing means for giving instructions for making the moving means move based on the reference point determined by the judging means.

In another aspect of the present invention, an ophthalmic apparatus including measuring means for measuring or examining an eye to be examined utilizing reflection of a luminous flux projected into the eye through a pupil, the ophthalmic apparatus comprises target projecting means for projecting an alignment target onto a cornea of the eye, target detecting means for detecting an image of the alignment target, photographing means for photographing an image of an anterior part of the eye, pupil position detecting means for detecting a position of the pupil by signals transmitted from the photographing means, measurement area defining means for defining a partition of an area necessary for measurement or examination based on the image of the alignment target detected by the target detecting means, calculating means for calculating coordinates where a dividing line of the area necessary for measurement or examination defined by said measurement area defining means crosses a periphery of the pupil detected by the pupil position detecting means, and judging means for determine whether or not the area necessary for measurement or examination is within the range of the pupil in accordance with vales calculated by the calculating means.

According to the present invention, even in a case of the eye to be examined of which alignment with respect to the corneal center may not be carried out due to the pupil condition, an alignment can be done with reference to the pupil position, and occurrence of measurement errors can be minimized. Therefor, even an inexperienced operator can easily perform an alignment without judging the pupil condition. Furthermore, referring to an apparatus for performing automatic alignment without an examiner, that a measurable area can be extend benefits an examinee.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
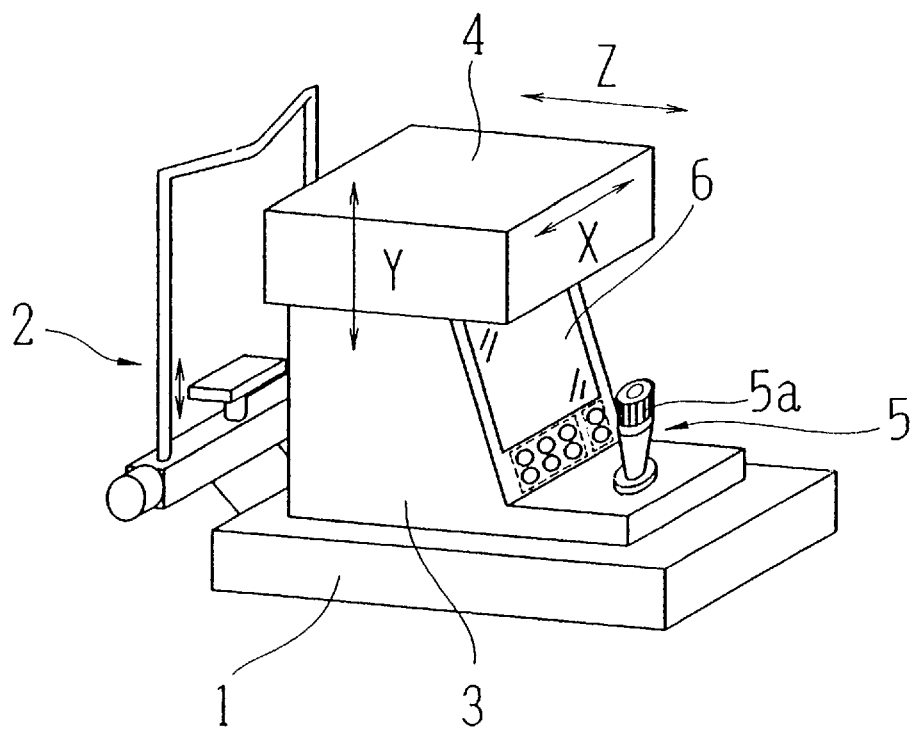
FIG. 1 is an overview of an automatic eye refractive power measuring apparatus of the preferred embodiment of the present invention.

A detailed description of one preferred embodiment of an ophthalmic apparatus embodying the present invention will now be given referring to the accompanying drawings. FIG. 1 is an overview of an automatic eye refractive power measuring apparatus of the preferred embodiment of the present invention.

Reference numeral 1 denotes a base provided with a face support unit 2 for supporting an examinee's face. 3 is a body and 4 is a measuring part containing an optical system as hereinafter described. 5 denotes a joystick for moving the body 3 and the measuring part 4. Responding to operations of the joystick 5, the body 3 slides along a horizontal plane of the base 1 in Z direction (back and forth direction) as well as in X direction (side to side direction). Responding to operations of a rotation knob 5a, the measuring part 4 moves in Y direction (up and down direction) relative to the body 3. In addition, the measuring part 4 is adjustable in X, Y and Z directions with respect to the body 3 so as to be operable upon automatic alignment. 6 denotes a TV monitor for displaying an image of an eye to be examined and information to be provided for an examinee.

Figure 2:
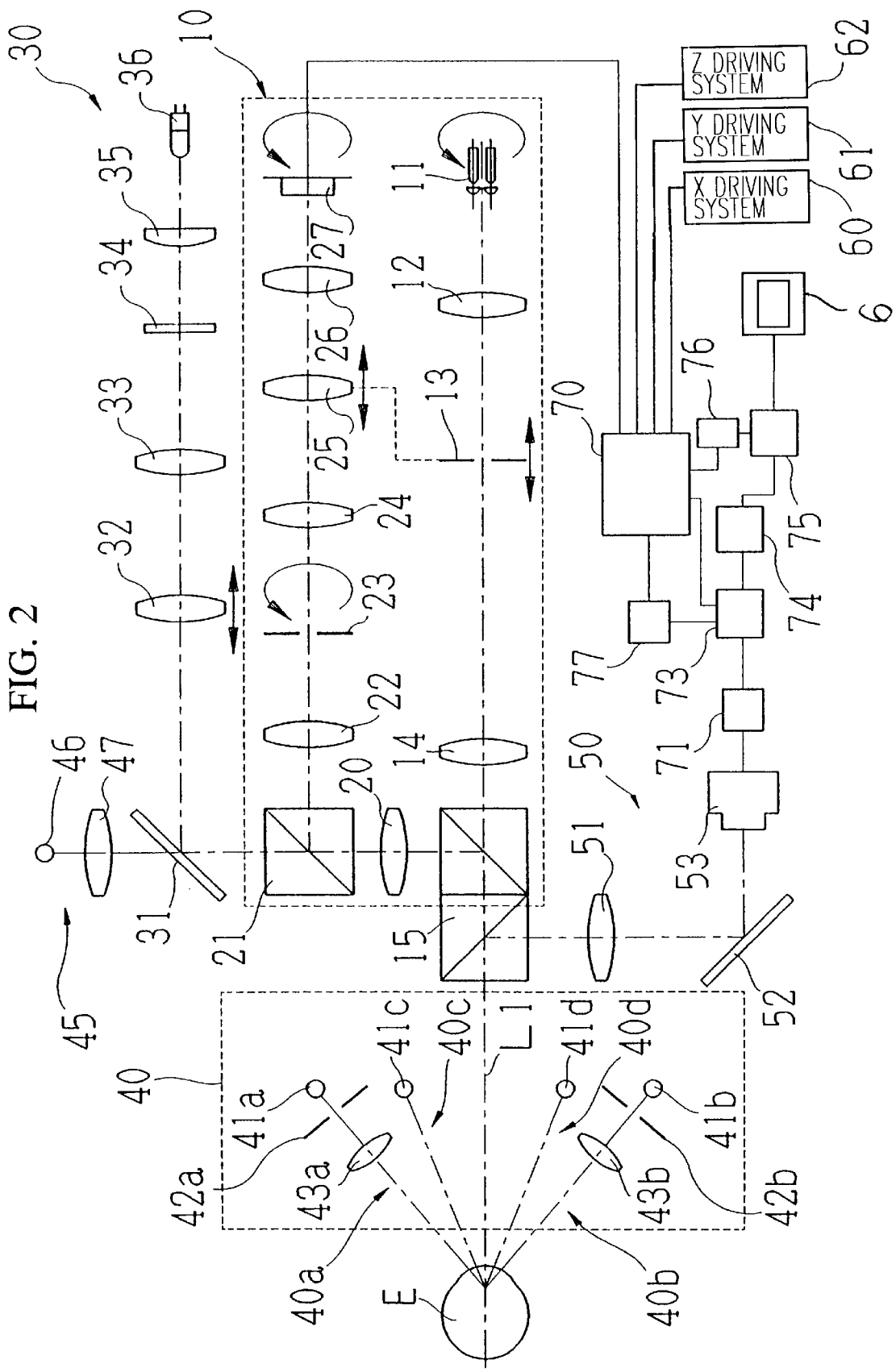
FIG. 2 is a view showing a schematic configuration of an optical system and a controlling system of the preferred embodiment of the present invention.

Next, a schematic configuration of the optical system and a controlling system of the apparatus will be described with reference to FIG. 2.

<optical system>

Reference numeral 10 denotes a measurement optical system. 11 denotes two light sources for measurement having their wavelength within a near infrared range which are arranged to be rotatable on an optical axis L1. 12 denotes a condenser lens, 13 denotes a movable target plate provided with a spot aperture, 14 denotes a projecting lens, 15 denotes a beam splitter, 20 denotes an object lens, 21 denotes another beam splitter, and 22 denotes a relay lens. 23 denotes a strip-shaped corneal reflection eliminating mask which is disposed at a conjugate position with respect to a cornea of the eye E. 24 denotes another relay lens, 25 denotes a moving lens which moves along with the target plate 13, 26 denotes an image forming lens and 27 denotes a photo-detector for measurement which rotates about an optical axis being synchronized with the light sources 11 and the corneal reflection eliminating mask 23.

Reference numeral 30 denotes a fixation target optical system. 31 is a dichroic mirror and 32 is a first relay lens which is capable of moving horizontally on the optical axis, and by this movement, the first relay lens 32 fogs the eye E. 33 is a second relay lens, 34 is a fixation target which is positioned at a focal point of the second relay lens 33, 35 is a condenser lens, and 36 is an illumination lamp.

Reference numeral 45 denotes a front target projecting optical system for projecting an alignment target from the direction of the visual line of the eye E. A point light source 46 emits a near infrared ray, and the near infrared ray successively passes through a rely lens 47, the dichroic mirror 31, the beam splitter 21 and the object lens 20, thereby made to be approximately parallel, then to be reflected at the beam splitter 15 so as to project an alignment target on the eye E for alignment in up and down direction as well as in side to side direction.

Reference numeral 40 denotes a target projecting optical system for detecting a working distance. The target projecting optical system 40 is provided with a pair of first target projecting optical systems 40a and 40b, and another pair of second target projecting optical systems 40c and 40d. The first target projecting optical systems 40a and 40b are arranged to be symmetrical to each other with respect to the optical axis L1, and the second target projecting optical systems 40c and 40d are, likewise, arranged to be symmetrical to each other with respect to the optical axis L1, but with a smaller angle relative to the eye E than that of the first target projecting optical systems 40a and 40b. The first target projecting optical systems 40a and 40b which include point light sources 41a and 41b for emitting near infrared rays, spot apertures 42a and 42b and collimator lenses 43a and 43b, project alignment targets of infinite distance onto the eye E by utilizing the luminous flux which are approximately parallel. On the other hand, the second target projecting optical systems 40c and 40d which include point light sources 41c and 41d for emitting near infrared rays, project alignment targets of finite distance by utilizing a divergent ray.

50 is an observing/target detecting optical system for observing an anterior part of the eye E and for detecting the alignment targets. The images of the alignment targets formed on the eye E as well as an image of the anterior part of the eye E illuminated by a near infrared ray emitted from a light source for illuminating anterior part of the eye E (not illustrated) are reflected at the beam splitter 15, pass through an object lens 51 and a mirror 52, so as to be photographed by a CCD camera 53.

<controlling system>

Output signal from the CCD camera 53 is digitized by an A/D converter 71, then captured by a flame memory 73. Having passed through a D/A converting circuit 74 and an image synthesizing circuit 75, the captured image is to be displayed on the TV monitor 6 in real time. Numeral reference 76 is a display circuit for generating alignment marks, graphics, textual information, and the like. Signals from the display circuit 76 is synthesized with picture signals from the CCD camera 53 in the image synthesizing circuit 75 so as to be displayed on the TV monitor 6. 77 denotes an image processing part to conduct predetermined processes to the images captured into the frame memory 73. A controller 70 detects a position of the image of the alignment target as well as a position of the pupil of the eye E under signals from the image processing part 77.

Reference numeral 60 denotes an X driving system for moving the measuring part 4 in X direction relative to the body 3, 61 denotes a Y driving system for moving the same in Y direction, and 62 denotes a Z driving system for moving the same in Z direction. Each of the driving systems is composed of a motor, a motor driving circuit, and the like.

Figure 3:
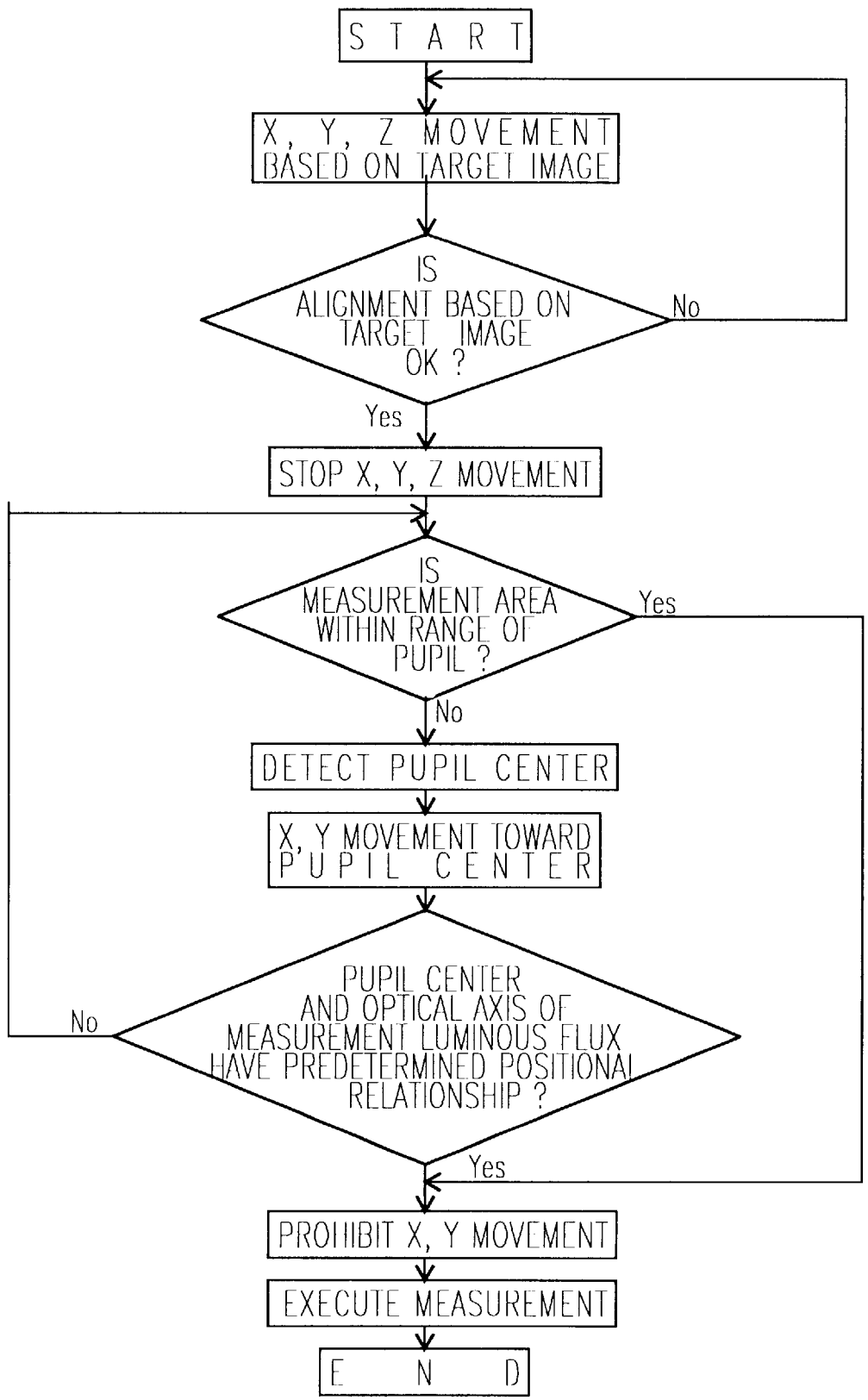
FIG. 3 is a flowchart for describing operations of the apparatus upon automatic alignment.

Hereinafter, operations of the apparatus having above-described configuration at the time of performing automatic alignment will be described. (See FIG. 3, the flow chart)

First, an examiner carries out a rough alignment by utilizing the joy stick 5 or the like with observing the TV monitor 6. Once the rough alignment is done and five target images, formed by the front target projecting optical system 45 and the target projecting optical system for detecting a working distance 40, are photographed by the CCD camera 53, the controller 70, under signals from the image processing part 77, extracts a target image 101 formed by the front target projecting optical system 45, and detects alignment conditions in terms of XY directions with reference to the detected image (that is to say with reference to the corneal vertex). To detect alignment conditions in terms of Z direction, the distance between target images 102a and 102b formed by the first target projecting optical systems 40a and 40b and the distance between target images 102c and 102d formed by the second target projecting optical systems 40c and 40d are to be compared. This is to utilize the characteristics of images of corneal reflection formed by an infinite-distance light and a finite-distance light. The height of an image of the corneal reflection formed by an infinite-distance light remains the same even if the working distance changes, while the height of an image of the corneal reflection formed by a finite-distance light varies responding to the change in the working distance (for the details of this relationship, see U.S. Pat. No. 5,463,430 corresponding to Japanese Patent Laid-Open No. HEI 6-46999).

The controller 70 triggers each of the driving systems on the basis of the alignment information obtained by detecting the targets, and moves the measuring part 4 in each direction to make alignment adjustment. Once respective alignment conditions in X, Y and Z directions are within predetermined acceptable ranges, the controller 70 stops each driving system. After confirming that the alignment conditions in X and Y directions, judging from the target image 101, are within the predetermined acceptable range, the controller 70 judges whether or not the measurement luminous flux can pass through the pupil of the eye E.

Hereinafter, the method of judging whether or not the measurement luminous flux can pass through the pupil of the eye E will be described. First, how to define a measurement area necessary for measurement will be mentioned. As an example, let the measurement area be a rectangle area 110 which is a square area surrounded by horizontal lines of M1 and M2 and vertical lines of M3 and M4. The measurement area actually required for measurement is a circle area. However, as long as the rectangle area 110 is defined to be tangent internally or externally to the circle area, it should be regarded as equal when making judgement whether or not the measurement luminous flux can pass through the pupil of the eye E. Besides, to define the measurement area as a rectangle area is advantageous for signal processing in terms of memory. To set the horizontal lines of M1 and M2 and the vertical lines of M3 and M4 which define the rectangle area, given that the diameter which the measurement optical system requires is 2.5 mm, the X and Y coordinates of respective lines are to be on the lines corresponding to ±11.25 mm from the optical axis L1.

Figure 4:
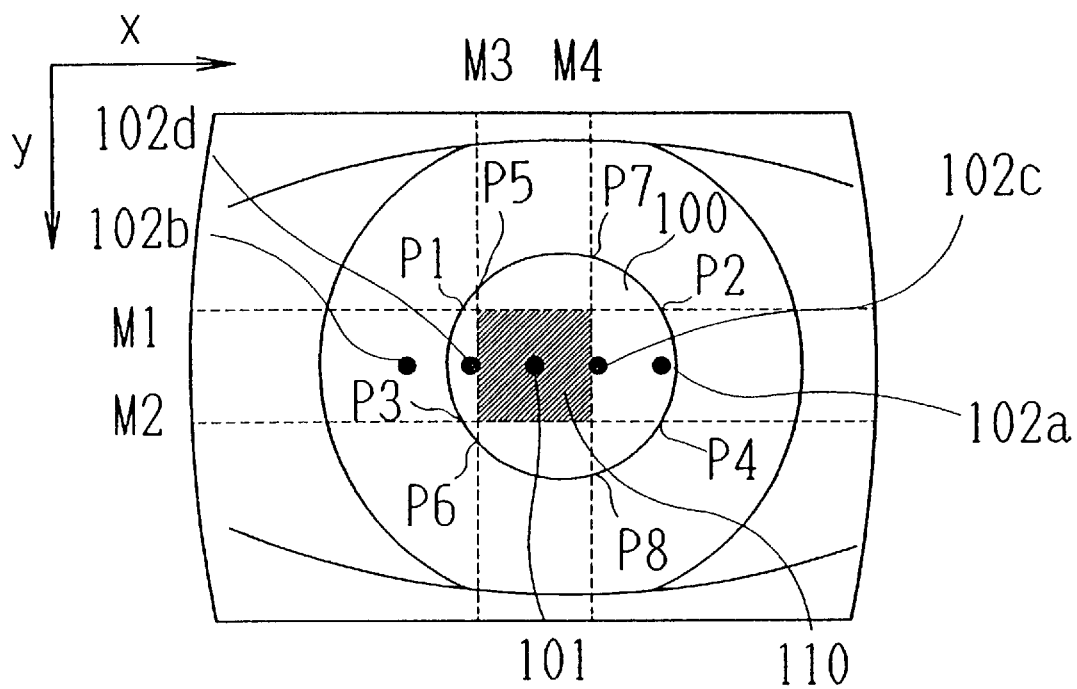
FIG. 4 is a view illustrating the way to define an area necessary for measurement and the way to determine wether or not the area is within a range of a pupil.

Next, the method of judging whether or not the rectangle area necessary for measurement is within the range of the pupil of the eye E will be described. As shown in FIG. 4, the coordinates at which the horizontal lines M1 and M2 respectively cross peripheries of the pupil 100 shall be P1, P2 and P3, P4. Likewise, the coordinates at which the vertical lines M3 and M4 respectively cross peripheries of the pupil 100 shall be P5, P6 and P7, P8. If the X coordinates of P1–P8 satisfy the condition given in the following expression, the rectangle area 110 can be regarded to be within the range of the pupil of the eye E. Although the Y coordinates of P1–P8 are not mentioned herein, it is also possible to make judgements with respect to the Y coordinates in a like manner.

$$P1 \leq P5 < P7 \leq P2, \text{ and } P3 \leq P6 < P8 \leq P4 \quad \text{(expression 1)}$$

Even in the case where the pupil diameter is relatively large, thus the pupil is partially covered by an upper eyelid, the coordinates of P5 and P7 are to be treated likewise in the same manner.

Furthermore, each of the coordinates can be obtained easily by fetching horizontal and vertical waveform from picture signals stored in the frame memory 73 and signal processing of differential processing or the like. Upon the detection, when each image of the corneal reflection interferes with the detection as picture noise, each point light source is to be turned on and off in turn and the timing of the target detection and the pupil position detection is to be staggered, so that each image can be easily distinguished from the other.

When the alignment based on the target image 101 (the confirmation that the alignment conditions in X and Y directions, judging from the target image 101, are within the predetermined acceptable range) is completed, and the alignment condition allows the measurement luminous flux to pass though the pupil, the controller 70 automatically executes (starts) the measurement.

Figure 5:
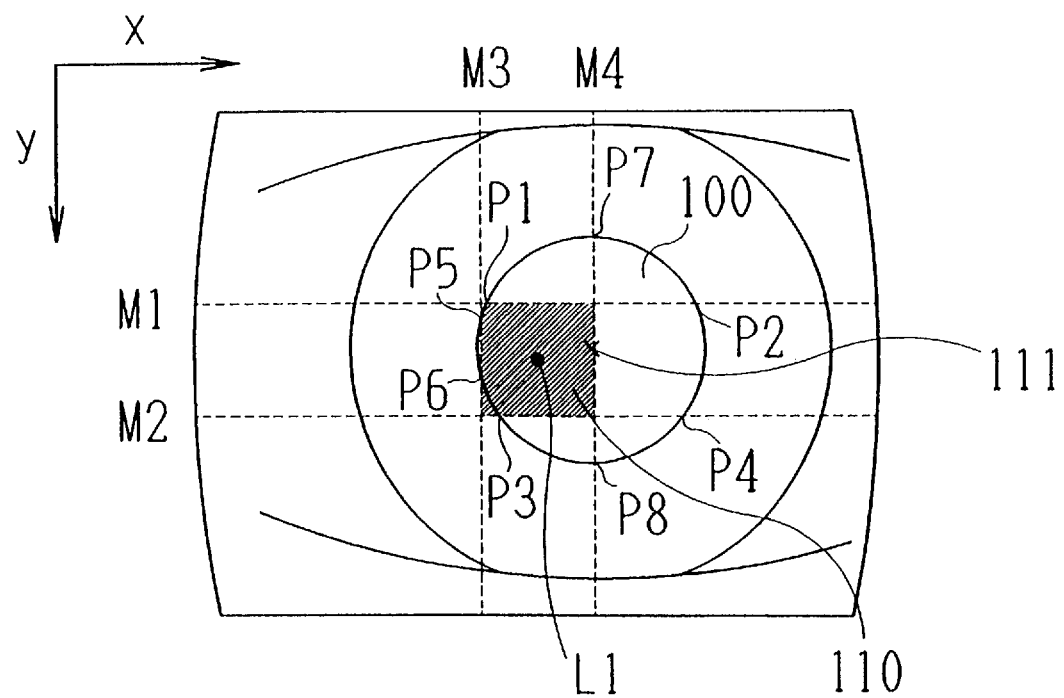
FIG. 5 is a view showing an example of a case where the area necessary for measurement is not within the range of the pupil due to the deviation between the corneal center and the pupil center.

On the contrary, if there is a deviation between the corneal center and the pupil center, and therefore the condition given in the above-mentioned expression (1) is not satisfied, as shown in FIG. 5 (target images are not illustrated therein), it is regarded that the alignment is not under acceptable condition for the measurement luminous flux to pass though the pupil. Accordingly, further alignment adjustment in X and Y directions is to be made with reference to the pupil position in order to bring the rectangle area 110 within the range of the pupil 100. In order to carry out this alignment, a direction in which the measuring part 4 is to be shifted is first to be obtained. For higher accuracy in measurement results, it is preferred that the deviation from the corneal center is as small as possible. For this reason, the rectangle area 110 (the optical axis L1) is made to be shifted toward the pupil center 111, yet kept within the range of the pupil 100. The coordinates of the pupil center 111 can be calculated from the coordinates of P1–P8 obtained in the aforementioned way; the X coordinates is obtained by seeking the center of the X coordinates of P1 and P2, or P3 and P4, and the Y coordinate is obtained by seeking the center of the Y coordinates of P5 and P6, or P7 and P8.

After having obtained the coordinates of the pupil center 111, the controller 70 drives the measuring part 4 (the optical axis L1) in X and Y directions toward the coordinates of the pupil center 111. As the apparatus regularly (at a fixed intervals) monitors whether the aforementioned rectangle area 110 is within the range of the pupil 100, once it is judged that the rectangle area 110 is within the range of the pupil 100, the apparatus stops the moving the measuring part 4 in X and Y directions and finishes the alignment. Thereafter, the measurement is to be executed.

As described above, it can be managed to bring the rectangle area 110 within the range of the pupil 100 in cases where the pupil diameter is relatively bigger than the rectangle area 110. On the contrary, when the pupil has a diameter smaller than the predetermined rectangle area 110, the condition given in the expression (1) can not be fulfilled. In such a case, when the pupil center 111 and the optical axis L1 are overlapped within a predetermined acceptable area, the movement in X and Y directions is made to be stopped, and the alignment is to be completed. Thereafter the measurement is to be started.

Next, an eye refractive power measurement will be mentioned. The measurement luminous flux emitted from the light sources 11 successively passes through the target plate 13, the projecting lens 14 and the like. After having been converged in the vicinity of the cornea, the measurement luminous flux reaches the fundus of the eye E. The target image reflected at the fundus of the eye E is passed through the area of the pupil necessary for the measurement and to be formed on the photo-detector 27 by successively passing through the object lens 20, the beam splitter 21, the relay lens 22, the corneal reflection eliminating mask 23, the relay lens 24, the moving lens 25 and the image forming lens 26. In case that the eye E has ametropia, the controller 70 moves the moving lens 25 as well as the target plate 13 to conjugate positions relative to the fundus of the eye E based on the signal of reflected luminous flux received by the photo-detector 27. Next, the controller 70 moves the first relay lens 32 so as to place the fixation target 34 and the fundus of the eye E at conjugate positions with respect to each other and further moves the first relay lens 32 so that appropriate amount of diopter is to be fogged. At this stage, the light sources 11 and the photo-detector 27 and the like are made to be rotated around the optical axis. During the rotation, in response to the signals from the photo-detector 27, the target plate 13 and the moving lens 25 are made to be moved. By detecting the amount of this movement, values of the refractive power in respective meridian directions are obtained, and by conducting predetermined processes to these values, the refractive power of the eye E can be obtained.

In some cases of the eye E, the measurement luminous flux may not satisfactory pass through the pupil of the eye if an alignment is made on the corneal center. Even in these cases, however, the measurement results can be obtained with reducing occurrence of measurement errors by performing an alignment in accordance with the aforementioned method; that is to say by bringing the area necessary for measurement into the range of the pupil. In addition, the method increases the possibility of achieving a measurement result when the pupil of the eye E is relatively smaller than the area necessary for the measurement. It should be noted, however, that the measurement results obtained in this way naturally includes errors in some degrees comparing with an eye refractive power based on the measurement results obtained by the alignment on the corneal center. Yet, to obtain the measurement results serves some functions. For example, when prescribing spectacles by performing a subjective examination, the measurement results, despite errors it contains, will be helpful information to make a first selection of a degree of a spectacle lens. In case that alignment is made, not on the center of the cornea but on a deviated position therefrom, it can be displayed along with the measurement results, so that an examiner becomes aware that the measurement results includes errors in some degrees.

Although an automatic alignment has been mentioned above, if the automatic alignment is not to be carried out, a guide mark, such as an arrow or the like, is to be displayed on the TV monitor 6 for bringing the area necessary for a measurement into the range of the pupil. When the alignment is completed, the examiner is to be informed of the completion of the alignment.

Figure 6:
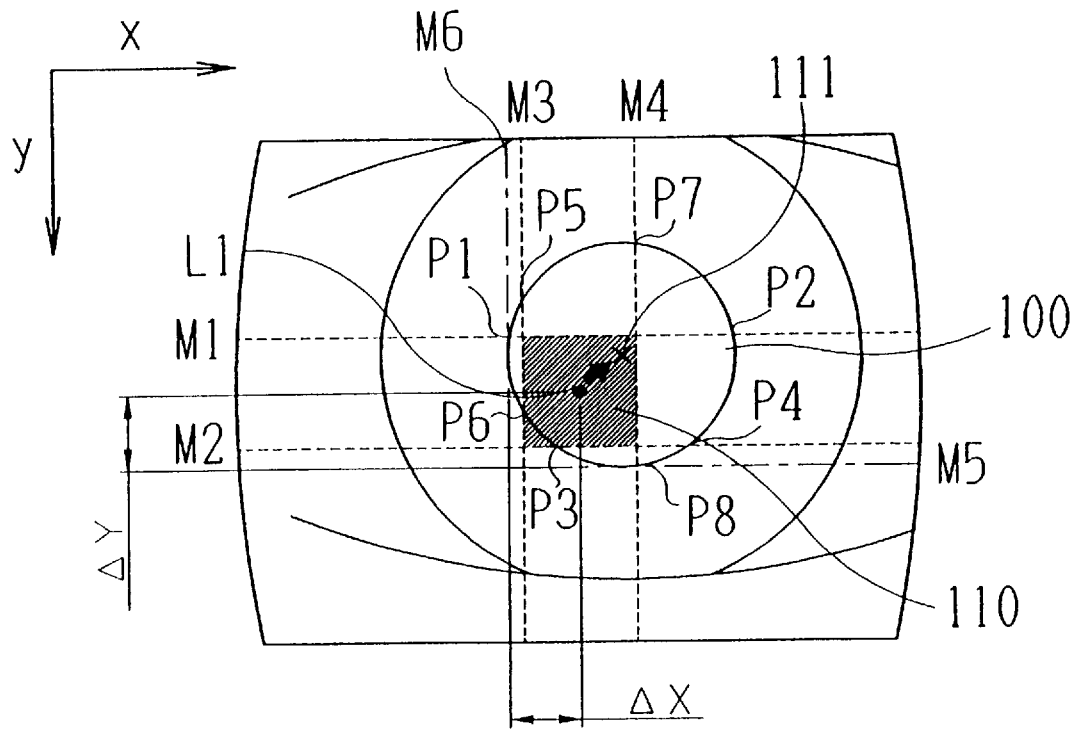
FIG. 6 is a view showing a variation to obtain the direction toward the pupil center.

In the alignment method described above, the coordinates of the pupil center is to be calculated, thereafter the measuring part 4 is guided (given directional instructions) thereto. Applying the following variation is also possible. As shown in FIG. 6, by utilizing picture information captured in the frame memory 73, a horizontal line M5 and a vertical line M6 are to be detected; each of the lines crosses a periphery of the pupil at a closer point (or two points having a predetermined interval therebetween) to the target image 101 (the center of the cornea) than the other horizontal or vertical line crosses a periphery of the pupil. Thereby, calculate each amount of the deviation $\Delta x$, $\Delta y$ from the optical axis L1. The gradient of the line which connects the optical axis L1 and the pupil center 111 is given in the following expression, so that the direction from the optical axis L1 toward the pupil center 111 can be acquired.

$-\Delta x/\Delta y$

The measuring part 4 is to be moved along the acquired direction in X and Y directions respectively. Once it is judged that the rectangle area 110 is within the range of the pupil 100, adjustment in X and Y directions is made to be stopped and the alignment is to be completed. If the pupil diameter is relatively smaller than the rectangle area 110, movement in Y direction is to be stopped at a point where the interval between P1 and P2 is approximately equal to the interval between P3 and P4. Likewise movement in X direction is to be stopped at a point where the interval between P5 and P6 is approximately equal to the interval between P7 and P8, thereafter the alignment is completed. That is to say, in case of that the pupil diameter is relatively small, alignment is made approximately on the pupil center.

Figure 7:
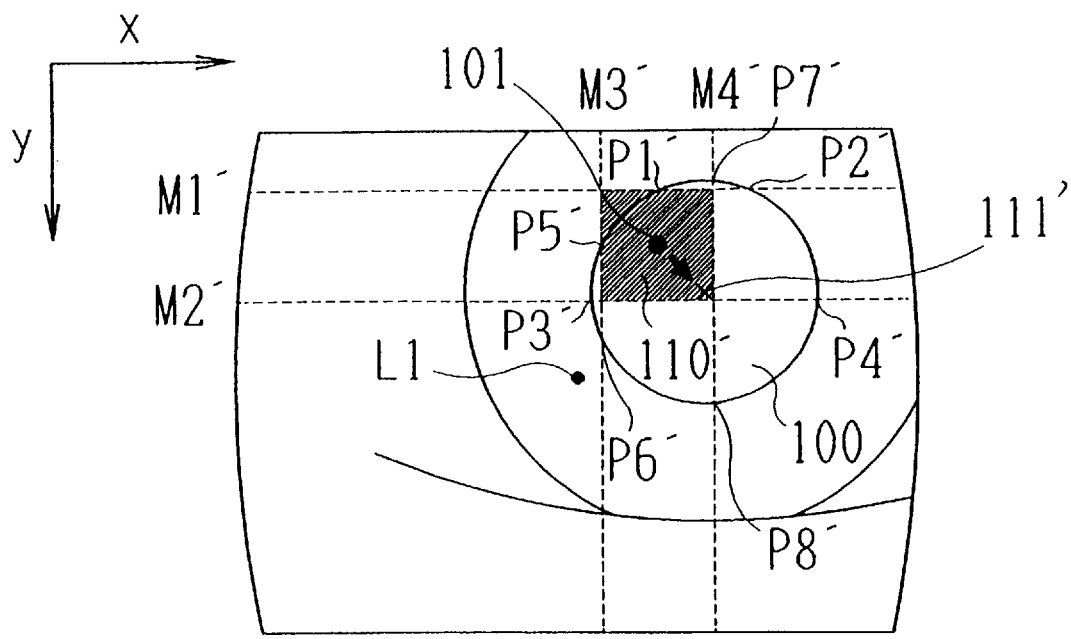
FIGS. 7 is a view illustrating judgement based on the image of the alignment target and the position of the pupil.

Upon guiding the measuring part 4, it is also possible to guide the measuring part 4 in accordance with the judgement whether or not the measurement luminous flux can pass through the pupil based on an alignment condition of the target image 101 before the time when the alignment based on the target image 101 (the corneal vertex) is completed. That is to say, even before aligning the optical axis L1 to the target image 101 (the corneal vertex), as shown in FIG. 7, an area with the center at the target image 101 surrounded by horizontal lines M1' and M2', and also vertical lines M3' and M4' to be defined as the rectangle area 110'. Whether the rectangle area 110' is within the range of the pupil 100 or not is judged by whether or not the coordinates of P1'–P8', where the horizontal lines M1' and M2', and also the vertical lines M3' and M4' respectively cross periphery of the pupil 100, satisfy the aforementioned expression (1). When it is judged that the rectangle area 110' is not within the range of the pupil 100, the pupil center 111' is to be calculated from the coordinates P1'–P8' just as in the aforementioned manner. When moving the center of the rectangle area 110' toward the pupil center 111' on the line therebetween, a position at which the rectangle area 110' comes into the pupil 100 (the center of the rectangle area 110') is to be calculated (by simulating the coordinates P1'–P8' upon the movement of the center of the rectangle area 110' toward the pupil center 111'). The alignment is completed when the optical axis L1 and the calculated center of the rectangle area 110' come to approximately the same position by moving the calculated center of the rectangle area 110' toward thereto. If the pupil of the eye E is smaller than the rectangle area 110', the center of the rectangle area 110' is to be moved toward the pupil center 111' instead. By this operation, movement of the measuring part 4 can be smoothly made, and therefore, the time spent on alignment is shortened.

In case that an examiner performs alignment manually, marks corresponding to objects to which movement is to be made are to be displayed on the TV monitor 6, so that the examiner can easily carry out the alignment (it will be easier to distinguish those marks from the target images and the like, if they are displayed in color).

In the preferred embodiment described above, the target for the alignment in X and Y directions is formed on the optical center of the cornea by projecting the approximately parallel luminous flux from the front side of the eye E. However, it is also possible to adopt a method, as in a cornea curvature measuring apparatus, to project ring patterns on the cornea of the eye E utilizing a divergent light. The optical center of the cornea can be calculated from the image of the ring patterns Based on the relationships between the corneal center calculated thereof and the positions of the pupil, alignment adjustment can be made. However, it should be noted that according to this method, there exist a slight deviation between the center of the ring patterns and the optical center of the cornea along with X and Y movement. The center of the cornea is to be calculated after having conducted corrective processes for this deviation.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is the claimed is:

1. An ophthalmic apparatus including measuring means for measuring or examining an eye to be examined utilizing reflection of a luminous flux projected into the eye through a pupil, the ophthalmic apparatus comprising:

moving means for moving said measuring means relative to the eye;

target projecting means for projecting an alignment target onto a cornea of the eye;

target detecting means for detecting an image of said alignment target;

photographing means for photographing an image of an anterior part of the eye;

pupil position detecting means for detecting a position of the pupil by signals transmitted from said photographing means;

judging means for determining a reference point for alignment based on information on the position of the pupil detected by said pupil position detecting means and the image of the alignment target detected by said target detecting means; and instructing means for giving instructions for making said moving means move based on the reference point determined by said judging means.

2. The ophthalmic apparatus according to claim 1, wherein said judging means determines the reference point for alignment based on whether or not the luminous flux within a predetermined area can pass through the pupil with respect to a position of the periphery of the pupil detected by said pupil position detecting means.

3. The ophthalmic apparatus according to claim 1, wherein said judging means determines the reference point for alignment based on whether or not the luminous flux within the predetermined area can pass through the pupil with respect to the position of the periphery of the pupil detected by said pupil position detecting means after having been carried out an alignment of said measuring means based on the image of the alignment target detected by said target detecting means.

4. The ophthalmic apparatus according to claim 1, wherein said moving means includes driving means for driving said measuring means to move and said instructing means includes controlling means for controlling said driving means.

5. The ophthalmic apparatus according to claim 1, the apparatus further comprising:

working distance detecting means for detecting an alignment condition relative to a direction of working distance of said measuring means toward the eye, monitoring means for monitoring whether or not the luminous flux within the predetermined area can pass through the pupil with respect to the reference point determined by said judging means; and measurement starting means for automatically staring a measurement when said measuring means is at a predetermined acceptable position according to a result detected by said working distance detecting means and a result monitored by said monitoring means.

6. The ophthalmic apparatus according to claim 1, wherein said judging means includes calculating means for calculating the reference point for alignment from information on the position of the image of the alignment target detected by said target detecting means and information on the position of the pupil detected by said pupil position detecting means.

7. The ophthalmic apparatus according to claim 1, wherein said instructing means includes displaying means for displaying a direction to which said moving means is made to move.

8. The ophthalmic apparatus according to claim 1 is an eye refractive power measuring apparatus.

9. An ophthalmic apparatus including measuring means for measuring or examining an eye to be examined utilizing reflection of a luminous flux projected into the eye through a pupil, the ophthalmic apparatus comprising:

target projecting means for projecting an alignment target onto a cornea of the eye;

target detecting means for detecting an image of said alignment target;

photographing means for photographing an image of an anterior part of the eye;

pupil position detecting means for detecting a position of the pupil by signals transmitted from said photographing means;

measurement area defining means for defining a partition of an area necessary for measurement or examination based on the image of the alignment target detected by said target detecting means;

calculating means for calculating coordinates where a dividing line of said area necessary for measurement or examination defined by said measurement area defining means crosses a periphery of the pupil detected by said pupil position detecting means; and judging means for determine whether or not said area necessary for measurement or examination is within the range of the pupil in accordance with values calculated by said calculating means.

10. The ophthalmic apparatus according to claim 9, wherein said measurement area of which partition is defined by said measurement area defining means is each of a rectangle and a circle shape.

11. The ophthalmic apparatus according to claim 9, the apparatus further comprising second calculating means to calculate the coordinates of the pupil center from the coordinates where the dividing line of said measurement area crosses the periphery of the pupil in cases where said judging means determines that the measurement area is not within the range of the pupil.

12. The ophthalmic apparatus according to claim 11, the apparatus further comprising:

moving means for moving said measuring means relative to the eye; and controlling means for controlling said moving means in order to move an optical axis of said measuring means toward said coordinates of the pupil center in case where said judging means determines that the measurement area is not within the range of the pupil due to the deviation between the corneal center and the pupil center.

13. The ophthalmic apparatus according to claim 11, the apparatus further comprising:

moving means for moving said measuring means relative to the eye; and controlling means for controlling said moving means in order to bring an optical axis of said measuring means in order to bring an optical axis of said measuring means at the same position as said coordinates of the pupil center within the predetermined acceptable range in case where said judging means determines that the measurement area is not within the range of the pupil owing to the fact that the pupil diameter is relatively smaller than the measurement area.

14. The ophthalmic apparatus according to claim 9, the apparatus further comprising:

third calculating means to calculate a direction of the pupil center relative to an optical axis of said measuring means in case where said judging means determines that the measurement area is not within the range of the pupil;

moving means for moving said measuring means relative to the eye; and controlling means for controlling said moving means in order to move the optical axis of said measuring means toward the direction of the pupil center calculated by said third calculating means.

15. The ophthalmic apparatus according to claim 9, the apparatus further comprising:

forth calculating means to calculate a center of the measurement area at the time when the measurement area is within the range of the pupil in case where said judging means determines that the measurement area is not within the range of the pupil;

moving means for moving said measuring means relative to the eye; and controlling means for controlling said moving means in order to bring an optical axis of said measuring means at approximately the same position as the center of the measurement area calculated by said fourth calculating means.

16. The ophthalmic apparatus according to claim 9 is an eye refractive power measuring apparatus.

* * * * *